(12) United States Patent
Georges et al.

(10) Patent No.: US 10,675,363 B2
(45) Date of Patent: Jun. 9, 2020

(54) SYSTEM AND METHOD FOR DIAGNOSIS OF ASTROCYTIC BRAIN TUMOR

(71) Applicants: Joseph Georges, Phoenix, AZ (US); Nikolay Martirosyan, Phoenix, AZ (US); Peter Nakaji, Phoenix, AZ (US)

(72) Inventors: Joseph Georges, Phoenix, AZ (US); Nikolay Martirosyan, Phoenix, AZ (US); Peter Nakaji, Phoenix, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 45 days.

(21) Appl. No.: 14/403,974

(22) PCT Filed: Jun. 3, 2013

(86) PCT No.: PCT/US2013/043877
§ 371 (c)(1),
(2) Date: Nov. 25, 2014

(87) PCT Pub. No.: WO2013/181655
PCT Pub. Date: Dec. 5, 2013

(65) Prior Publication Data
US 2015/0104395 A1    Apr. 16, 2015

Related U.S. Application Data

(60) Provisional application No. 61/654,438, filed on Jun. 1, 2012.

(51) Int. Cl.
*A61K 49/00* (2006.01)
*G01N 33/574* (2006.01)

(52) U.S. Cl.
CPC ... *A61K 49/0041* (2013.01); *G01N 33/57407* (2013.01)

(58) Field of Classification Search
None
See application file for complete search history.

(56) References Cited

U.S. PATENT DOCUMENTS

| 4,444,879 A * | 4/1984 | Foster | G01N 33/545 422/400 |
| 5,589,936 A * | 12/1996 | Uchikawa | G02B 21/002 356/450 |
| 2004/0082863 A1* | 4/2004 | McGreevy | A61B 1/313 600/476 |
| 2007/0025997 A1* | 2/2007 | Nagavarapu | C07K 16/2851 424/155.1 |

OTHER PUBLICATIONS

Kircher et al. A multimodal nanoparticle for preoperative magnetic resonance imaging and intraoperative optical brain tumor delineation. 2003 Cancer Res. 63: 8122-8125.*
Nimmerjahn et al. In vivo labeling of cortical astrocytes with sulforhodamine 101 (SR101). 2012 Cold Spring Harb Protoc. 3: 326-334. Published Mar. 1, 2012.*
Kubo et al. Clinicopathological study of oligodendroglioma with special reference to immunohistochemical investigation. 1988 No Shinkei Geka 16: 1029-1035. Article in Japanese. English abstract provided.*
Behbahani et al. Primary central nervous system t-cell lymphoma of the brain. 2011 The Open Neurosurgery Journal 4: 62-65.*
Chertok et al. Polyethyleneimine-modified iron oxide nanoparticles for brain tumor drug delivery using magnetic targeting and intra-carotid administration. 2010 Biomaterials 31: 6317-6324.*
Appaix et al. Specific in vivo staining of astrocytes in the whole brain after intravenous injection of sulforhodamine dyes. 2012 PLoS One 7: e35169. 13 pages. Published online Apr. 11, 2012.*
Supplementary European Search Report dated Jan. 28, 2016 for European Patent Application No. 13797004.
Georges et al., "Rapid diagnosis of human astrocytic tumors using sulforhodamine 101", J. Journal of Nuclear Medicine, vol. 51, No. Suppl. 1, Feb. 1, 2013 (Feb. 1, 2013), p. 9.
Kafitz et al., "Developmental profile and properties of sulforhodamine 101-Labeled glial cells in acute brain slices of rat hippocampus", Journal of Neuroscience Methods, Elsevier Science Publisher B.V., Amsterdam, NL, vol. 169, No. 1 Dec. 4, 2007 (Dec. 4, 2007), pp. 84-92.
Gupta, M., et al. "Clarifying the Diffuse Gliomas: An Update on the Morphologic Features and Markers that Discriminate Oligodendroglioma from Astrcytoma", American Journal of Clinical Pathology, vol. 124, No. 5, Nov. 1, 2005 (Nov. 1, 2005), pp. 755-768.
The International Search Report and Written Opinion dated Nov. 5, 2013 for International Application No. PCT/US2013/043877.
Lee, J et al., "Non-invasive quantification of brain tumor-induced astrogliosis", BMC Neuroscience, 2011, vol. 12, Issue 9; abstract; figure 1, Results and Discussion; pates 2, 5 and 6.
Nimmerjahn, A. et al., "Sulforhodamine 101 as a specific marker of astroglia in the neocortex in vivo", Nature Methods, Sep. 29, 2004, vol. 1, No. 1; abstract; last paragraph, p. 2 to second paragraph, p. 3.
Commins, DL "Pathology of primary central nervous system lymphoma", Neurosug Focus, Nov. 2006, vol. 21, No. 5; first column, second paragraph, second column, second paragraph; p. 4.

(Continued)

*Primary Examiner* — Jennifer Lamberski
(74) *Attorney, Agent, or Firm* — Qurales & Brady LLP; Yakov Sidorin; Gavin Milczarek-Desai

(57) ABSTRACT

Methods and systems for distinguishing an astrocytic human brain rumor from a non-astrocytic human brain tumor (FIG. 4). In one embodiment a method includes the steps of staining tumor tissue from a subject suspected of having a brain tumor with SR101 and visualizing the tissue stained with SR101 with a fluorescence imaging device to confirm an astrocytic or non-astrocytic tumor type. Advantageously, rumor tissue from a subject is stained ex vivo, and the staining and visualizing steps are performed intraoperatively so as to guide the surgeon and thereby minimize or eliminate the need for a subsequent surgery.

5 Claims, 7 Drawing Sheets

(56) References Cited

OTHER PUBLICATIONS

Feindel, W et al. "Intracarotid Fluorescein Angiography: A New Method for Examination of the Epicerebral Circulation in Man", Journal of the Canadian Medical Association, Jan. 7, 1967, vol. 96, No. 1; abstract.

* cited by examiner

SYSTEM AND METHOD FOR DIAGNOSIS OF ASTROCYTIC BRAIN TUMOR

CROSS-REFERENCE TO RELATED APPLICATIONS

This Application is a 371 application of PCT/US2013/043877 filed Jun. 3, 2013, which claims priority to U.S. Provisional Patent Application Ser. No. 61/654,438 filed Jun. 1, 2012, incorporated by reference herein in its entirety.

BACKGROUND OF THE INVENTION

Description of the Related Art

Surgical tumor resection is the frontline treatment for numerous cancers, including intrinsic brain tumors. Intraoperative histopathological diagnosis guides the surgical resection strategy. For over 100 years the frozen section has remained the method of choice for obtaining this pathological diagnosis. Although useful, this technique produces artifacts and provides only limited, non-specific information about the tissue based on its morphology and cellular architecture. The inability of the frozen section to provide rapid and specific information can limit the development of definitive intraoperative surgical plans.

Instead, clinical teams wait for post-operative antibody staining of biopsied tissue for identification of specific molecular markers, a process which in practice often requires 24-72 hours. On occasion, a mistaken intraoperative diagnosis can result in premature termination of surgery, resulting in an incomplete resection. This may have a negative impact on prognosis and require additional surgical intervention. For other tumor types, non-surgical therapeutic approaches are the most successful, and misdiagnosis can place patients at greater risk of complications and side effects from unnecessary resection. Furthermore, inaccuracy and delay in diagnosis can increase patient anxiety and health care costs.

Advances in molecular and cellular imaging are proving increasingly effective in characterizing tissues for researchers. However, application of many of these advanced imaging techniques to clinical pathology remains rudimentary or of unknown utility.

SUMMARY OF THE INVENTION

The disclosure herein relates to methods and systems for distinguishing an astrocytic human brain tumor from a non-astrocytic human brain tumor. In one embodiment, a method includes the steps of staining tumor tissue from a subject suspected of having a brain tumor with SR101 and visualizing the tissue stained with SR101 with a fluorescence imaging device to confirm an astrocytic or non-astrocytic tumor type.

Advantageously, tumor tissue from a subject is stained ex vivo, and the staining and visualizing steps are performed intraoperatively so as to guide the surgeon and thereby minimize or eliminate the need for a subsequent surgery.

Additional features and advantages of the invention will be forthcoming from the following detailed description of certain preferred embodiments when read in conjunction with the accompanying drawings.

DESCRIPTION OF THE PREFERRED EMBODIMENTS

Figure 1:
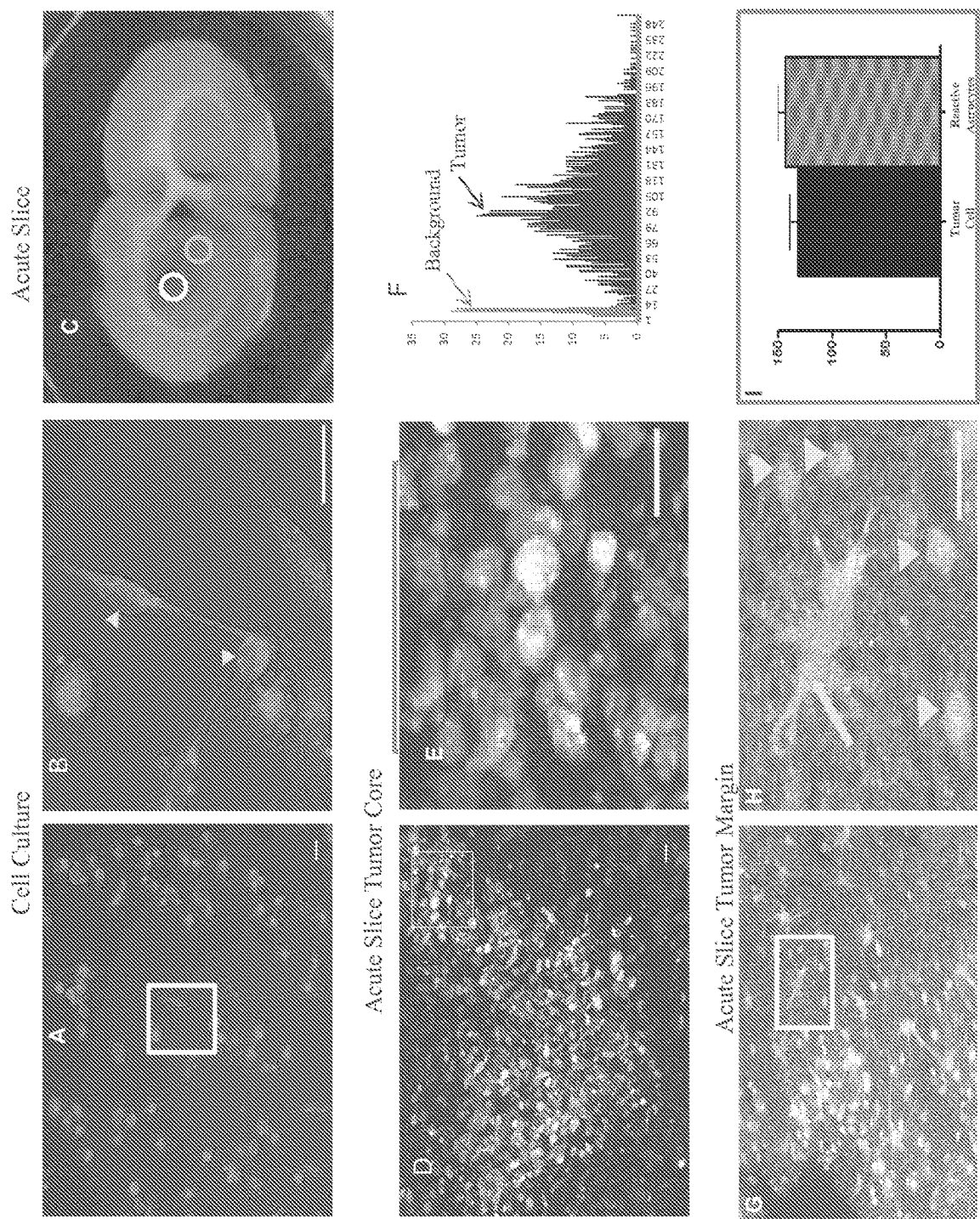
FIG. 1 depicts results showing that non-fixable SR101 labels human astrocytoma cells in culture and identifies tumor core and margin in rodent xenografts. U251 Astrocytoma Cell Culture (A-B). (A) DIC image with fluorescent overlay of human U251 astrocytoma cells incubated with SR101. (B) Inset showing cytoplasmic filling of cells and delineation of cell nuclei (arrowheads). Acute slices from rodents intracranially implanted with U251 cells (C-H). (C) Acute slice containing U251 derived tumor. Representative core and margin regions identified by white circle and gray circle respectively. (D) Confocal fluorescence image of SR101-labeled tumor core. (E) High magnification of inset showing typical morphology of U251 cells. (F) Histogram of SR101 fluorescence distribution in E between tumor core and background (x axis is pixel count; y axis is fluorescence intensity). Note the clear distinction in mean fluorescence intensity (MFI) between tumor (102.84) and background (8.74). (G) Image of tumor margin with SR101 labeled cells. (H) Inset of morphologically identified reactive astrocyte (arrow) surrounded by glioma cells (arrowheads) near the tumor margin. (I) Mean fluorescence intensity (y axis) of U251 cells and reactive astrocytes normalized to background (n=9 optical sections from 3 acute slices). Note no statistically significant difference in MFI between the two cell types. Scale bar equals 20 um.

Aspects of the embodiments described herein involve the use of live-cell imaging techniques using physiological fluorophores that could revolutionize the current standard of care by providing more rapid and specific final pathological diagnoses.

Glioblastoma multiforme (GBM), grade IV astrocytoma, is the most common subtype of astrocytoma, with a median survival of only 11-15 months. Patient survival is directly related to the extent of GBM tumor resection which is guided by intraoperative identification of tumor margins. In contrast, for other central nervous system (CNS) tumors, such as CNS lymphoma, definitive resection is contraindicated; the most common surgical approach is diagnostic biopsy alone. Distinguishing between these two types of tumors is therefore critical for determining the course of therapeutic action. Currently, morphological approaches alone are often insufficient and necessitate antibody staining of resected brain tissue. GBM and lymphoma are differentiated by immunostaining a patient biopsy specimen. Glial fibrillary acidic protein (GFAP) positivity supports the diagnosis of GBM, whereas CD20 positivity identifies CNS B-cell lymphoma. While effective, this method has heretofore been too slow to be completed during surgery.

Sulforhodamine 101 has been widely used in neuroscience research to identify astrocytes in live tissue. Although the mechanism of this staining is incompletely understood, numerous reports have verified the stain works rapidly on live cells to specifically label astrocytes. SR101 labeling resembles GFAP, and it has been shown to label rodent astrocytoma cells in culture.

In further illustration of certain embodiments, the examples below describe the use of the fluorophore Sulforhodamine 101 (SR101) as a marker for astrocytoma, the most common histological type of primary brain tumor, for distinguishing astrocytic tumor subtypes, and for tumor margin definition.

EXAMPLES

Cell culture:

We acquired human glioma cell line U251 and human CNS lymphoma cell line MC116 from ATCC. Cells were maintained in culture with DMEM media supplemented with 10% FBS, and RPMI media supplemented with 20% FBS respectively (all from Invitrogen, Grand Island, N.Y.). Cells were grown at 37° C. in a humidified incubator under 5% $CO_2$.

In Vitro SR101 Labeling:

We labeled U251 glioma cells by seeding a collagen-coated glass-bottom dish (MatTek) with 100,000 cells. After 24 hours, media was replaced with aCSF containing 5 uM SR101 (Sigma) for 20 minutes, followed by two 5 minute washes with standard aCSF.

Animals:

Fifteen male Crl:NIH-Foxn1$^{nu}$ rats (5 weeks age) were obtained from The Charles River Laboratories International, Inc. (Wilmington, Mass.). Experiments were performed in accordance with the guidelines and regulations set forth by the National Institutes of Health Guide for the Care and Use of Laboratory Animals and were approved by the Institutional Animal Care and Use Committee of the Barrow Neurological Institute and St. Joseph's Hospital and Medical Center.

Intracranial Implantation:

Animals were anesthetized by intramuscular injection of a mixture of 10 mg/kg xylazine and 80 mg/kg ketamine (Wyeth, Madison, N.J.) and placed in a small animal stereotactic headframe (Model 900, David Kopf Instruments, Tujunga, Calif.). A 10-mm incision was made starting between the animal's eyes, exposing bregma. A bur hole was made 3.5 mm lateral to bregma. U251 or MC116 cells were infused at a depth of 4.5 mm below the surface of the brain after the syringe (Hamilton) was advanced 5.0 mm to create a 0.5-mm pocket. The cell suspension was infused using a UMP3-1 UltraMicroPump microinjector (WPI, Sarasota, Fla.) set to a volume of 10 μL with an infusion rate of 3.00 μL/minute. The needle was withdrawn 2 minutes after the injection to minimize backflow of the cell suspension. The bur hole was covered with bone wax and the skin incision was sutured.

Acute Slices:

Twenty days post-implantation, rats were deeply anesthetized using the xylazine/ketamine mixture as described previously. Animals were rapidly decapitated, brains were removed, and coronal cortical slices (350 μm thick) were cut on a vibratome (Trent's aCSF protocol). Slices were then incubated at room temperature in aCSF containing 5 uM SR101 for 20 minutes followed by a 10 minute wash in aCSF.

Co-Labeling:

Xenograft acute slices were incubated with the fixable version of SR101 (Texas Red Hydrazide; Sigma), washed at room temperature, and fixed with 4% paraformaldehyde for 12 hours at 4 degrees C. Slices were then rinsed in phosphate buffered saline, permeabilized with 0.3% triton, and blocked with CAS block (Invitrogen) (reference Pierre's paper). GBM xenograft slices were incubated 12-hours in anti-GFAP primary antibody (Millipore; 1:500), and Lymphoma sections were incubated 12-hours in anti-CD20 primary antibody (Millipore; 1:250). Sections were then rinsed and incubated with AlexaFluor488 secondary antibody (Invitrogen), followed by nuclear counterstaining with Dapi (Invitrogen). Fluorescently labeled sections were mounted on slides with vectashield (Vector labs) and No1.5 coverslips (VWR).

Stereology:

We randomly selected one rostral, midline, and caudal acute slice from each brain containing tumor incubated with fixable SR101. Glioma slices were immunofluorescently stained for GFAP, and slices containing lymphoma were stained for CD20. Ten randomly selected 150 um$^2$ tumor areas in each slice were optically sectioned to 50 um with a Zeiss 710LSM. The first 5 um of each image stack was discarded to minimize counts from cells damaged during sectioning. A maximum intensity projection image was generated from the remaining 45 um, and a stereology dissector was overlaid onto the image. Cells within the dissector, and those in contact with its left and bottom edges were counted for either GFAP or CD20 positivity, and for SR101 positivity. The percent overlap between immunostaining and SR101 positivity was calculated. A t-test, with significance set at less than or equal to 0.05, was used to determine if there was a difference between antibody and SR101 labeled cells in glioma and lymphoma models.

In Vivo Labeling:

Twenty days post-implantation, rats were deeply anesthetized using the previously described ketamin/xylazine mixture. The rats were then intra-arterially injected with Texas red hydrazide. Two hours post-injection brains were perfused, fixed, and sectioned on a cryostat. Sections were mounted on slides and imaged with a Zeiss LSM 710 confocal microscope.

Human Samples:

This research was approved by the institutional review board at St. Joseph's Hospital and Medical Center and all surgery was performed at the Barrow Neurological Institute. All subjects were consented pre-operatively for participation. Samples were obtained at the time of craniotomy from within the tumor mass at a location determined to be safe by the surgeon. The samples, averaging 4×2×2 mm in size, were transferred into ice-cold artificial cerebrospinal fluid (aCSF) containing 5 uM SR101. Samples were then transferred from the operating room to the laboratory, rinsed with aCSF (10 minutes), and immediately imaged.

Imaging:

SR101-labeled samples were placed in uncoated No. 1.5 glass-bottom dishes and positioned on the stage of a Zeiss 710 laser scanning confocal microscope equipped with a 40x/1.2NA water emersion objection. We imaged SR101 by exciting the fluorophore with a 561 nm diode laser and collecting 595 nm-625 nm emission. The confocal aperature was set to Airy unit for all imaging. The laser and gain values were set to fill the dynamic range of the photomultiplier tube, and the frame size was set to sample at nyquist. Images were collected in 8 and 12 bit format absent of non-linear processing. An unstained adjacent tissue sample was imaged with each sample. In some cases, large field-of-view tiled and optically sectioned images were rapidly acquired using a Zeiss line-sweeping confocal microscope. Frame size for this system was fixed to 512×512 by a linear charged coupled device (CCD) array.

Sulforhodamine 101 Labels Human Astrocytoma Cells and Reactive Astrocytes

SR101 is a red fluorescent dye that has been repeatedly used in neuroscience research to rapidly and specifically label astrocytes. To investigate the potential for this fluorophore to similarly identify human astrocytoma cells, we first applied SR101 to human astrocytoma cell line U251 in culture. After brief incubation and differential inference contrast imaging with fluorescence overlay, we found that the fluorophore filled the cytoplasm of the cultured cell and clearly delineated cell nuclei (FIGS. 1A, 1B). This prompted us to explore SR101's ability to label astrocytoma cells in an animal model.

We intracranially implanted human astrocytoma cells into the caudate-putamen of nude rats using a model known to consistently produce well-characterized tumors (tomoko, sontheimer). Following 4 weeks of tumor growth, we produced acute slices from the animals (FIG. 1C). Slices were then rapidly treated with SR101 by bath application for 20 minutes and live cell confocal images taken. Images taken of tumor cores revealed cells markedly labeled with SR101 which were clearly distinguished from low level background staining (FIGS. 1D, 1E, 1F).

Rapid identification of the tumor core is important to assist diagnosis. However, it is the identification of the tumor margin that is ultimately critical for guiding astrocytoma resection. In this regard we again used confocal microscopy to image tumor margins within the acute slices treated with SR101. SR101 staining revealed distinct tumor margins that contained SR101 positive astrocytoma cells and reactive astrocytes (FIGS. 1G, 1H). After quantification of fluorescence intensity from astrocytoma cells and reactive astrocytes, we found mean fluorescence intensity did not differ between these two cell types (FIG. 1I). However, reactive astrocytes could be easily distinguished based on their distinct morphologies (FIG. 1H). These results show that human SR101 staining is highly effective at rapidly identifying not only astrocytes, but astrocytoma tumor cells in cell culture and in animal models, and an effective tool to define the tumor margin.

Fixable SR101 Labels GFAP-Positive Human Astrocytoma Cells and Reactive Astrocytes.

We next compared the staining localization of SR101 to GFAP antibody staining, which is the clinical standard for identification of astrocytomas. Since SR101 is not amenable to fixation, we used a fixable version of SR101 (Texas Red Hydrazide) for these experiments. The staining pattern of this fluorophore has been well-documented to mimic SR101's staining pattern. We incubated acute slices from astrocytoma xenografts with fixable-SR101, fixed the slices, and counterstained with GFAP and DAPI.

Confocal images taken from tumor core regions showed numerous cells filled with fixable-SR101 that were GFAP positive (FIGS. 2A-2D). Some cellular processes stained less intensely for fixable-SR101 than GFAP (Arrows 2A, 2B, 2D). Merged images from the tumor core revealed the majority of cells were positive for both fixable SR101 and GFAP.

Figure 2:
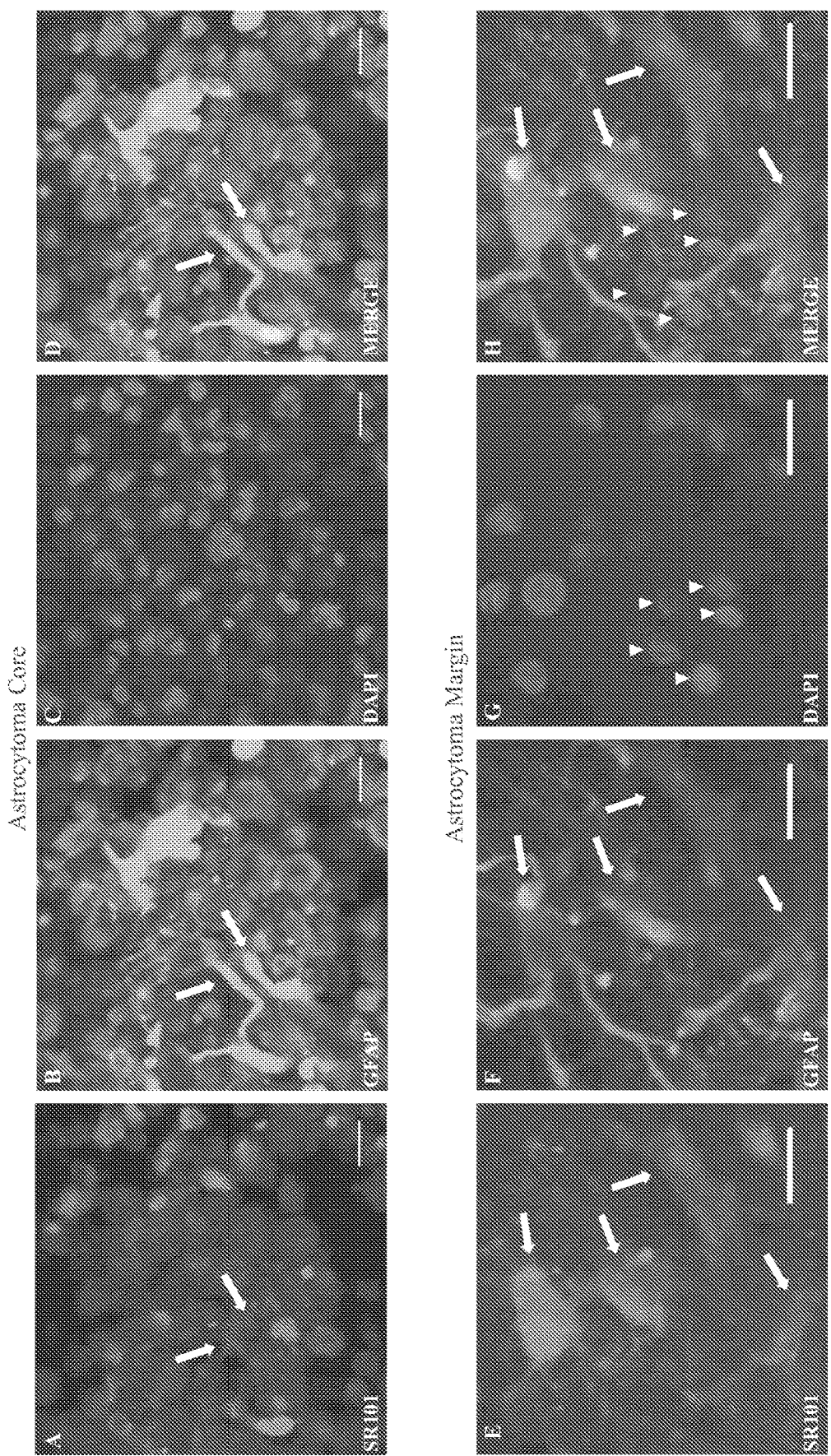
FIG. 2 depicts results showing that fixable SR101 colocalizes with the astrocytic marker GFAP. Confocal imaging of rodent xenograft acute slices incubated in the fixable version of SR101. Following incubation slices were fixed and stained with GFAP and Dapi. Images taken from the core of the astrocytoma (A-D). Fixable SR101 fills the cell bodies of GFAP-positive cells in the tumor core, and weakly fills astrocytic processes (arrows). Note the significant overlap of GFAP, DAPI and SR101 in the merged image. Images taken from the margin of the astrocytoma (E-H). Fixable SR101 fills cell bodies of GFAP-positive cells at the tumor margin. Solid arrows identify SR101 and GFAP positive cells. Note the appearance of DAPI positive cells (arrowheads) unlabeled by SR101 or GFAP that are selectively observed at the astrocytoma margin. Scale bar equals 20 um.

Reactive astrocytes densely populate regions outside of brain tumors, and are positive for SR101 and GFAP. Since these cells are SR101 positive, it is important to differentiate them from SR101-positive tumor cells. Therefore, we compared the staining pattern of fixable-SR101 to GFAP in these cells. We imaged brain regions adjacent to astrocytomas and found cells with similar staining patterns for fixable-SR101 and GFAP (FIGS. 2E, 2F). However, more thorough labeling of membrane processes was apparent with GFAP labeling. Cells in the peripheral regions contained extensive membrane projections that could be differentiated from cells within the tumor core that lacked this feature. We identified additional cells in these regions by staining with DAPI (FIG. 2G), and observed groups of cells negative for both fixable-SR101 and GFAP (FIGS. 2G, 2H arrows). This indicated the presence of a mixed cell population which is typical for regions outside the tumor core. Together, these data show that tissue incubated with fixable-SR101 stains in a manner that co-localizes with GFAP, confirming that SR101-positive cells are the GFAP positive astrocytoma cell population, and fixable-SR101 provides sufficient morphological information to differentiate astrocytoma cells from reactive astrocytes.

SR101 Differentiates Astrocytoma from Lymphoma.

Definitive intraoperative differentiation of astrocytoma from lymphoma is not possible in current clinical practice. This distinction is crucial since astrocytoma patients benefit from maximal tumor resection while lymphoma patients are best treated without resection. Currently, these tumors are clinically differentiated by two-stage antibody staining with GFAP and CD20. GFAP positivity supports a diagnosis of astrocytoma, while CD20 positivity supports a lymphoma diagnosis. This method typically requires a minimum of 24 hours to provide a diagnosis in practice, and is therefore too slow to provide intraoperative information.

We explored the feasibility of using SR101 to provide rapid diagnostic information to differentiate these tumors. Since we found SR101 to specifically label astrocytoma cells in rodent xenografts, we tested its actions on a human CNS lymphoma animal model. We produced acute slices from nude rats intracranially implanted with human CNS lymphoma cells, and incubated the slices with SR101. Confocal imaging of the slices showed minimal SR101 signal from lymphoma regions.

Figure 3:
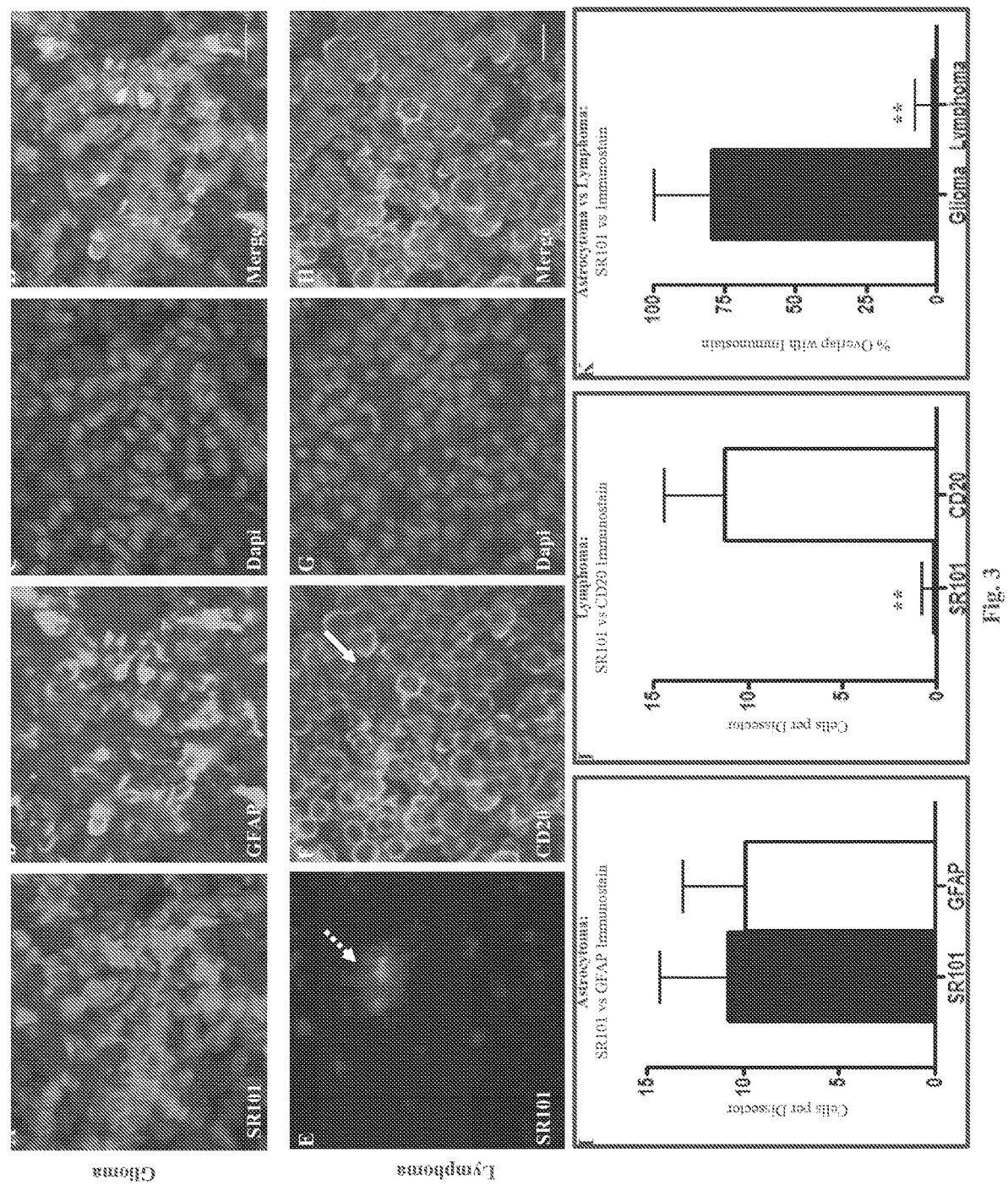
FIG. 3 depicts results showing that SR101 rapidly differentiates human astrocytoma from CNS lymphoma in rodent xenografts. Confocal imaging of acute slices taken from xenograft animals implanted with astrocytoma cells (U251) (Top) or lymphoma cells (MC116) (Middle). Slices were stained with fixable SR101 and specific markers for Astrocytoma (GFAP) or Lymphoma (CD20). Nuclei were counterstained with DAPI. Top: Region from U251 astrocytoma acute slice incubated with fixable SR101 and counterstained with GFAP and DAPI (A-D). Middle: (E) SR101 labels a single cell (dashed arrow) in a MC116 xenograft lymphoma region. (F) CD20 immunostaining labels lymphoma cells, but does not label region containing SR101-positive cell (solid arrow). (G) DAPI counterstain of cell nuclei in field of view. (H) Merged lymphoma image indicating poor colocalization of SR101 and CD20. Scale bar equals 20 um. Bottom: Confocal stereology of acute slices (see Methods). (I) Number of SR101 and GFAP-positive cells present in U251 xenograft astrocytoma regions are not statistically different ($p<0.01$*). (J) Number of SR101 and CD20-positive cells present in MC116 xenograft lymphoma regions are highly statistically different ($P<0.01$*). (K) SR101 significantly overlaps with GFAP positive astrocytoma cells (79.6%) compared with CD20 lympoma cells (1.97%) ($P<0.01$).

Next, we incubated acute slices from astrocytoma and CNS lymphoma animal models with fixable-SR101 and quantified the staining localization to GFAP for astrocytoma slices and CD20 for lymphoma slices. We adapted standard stereology approaches to quantify tumor cells labeled with fixable-SR101 and GFAP or CD20 antibodies. Fixable-SR101 labeled the majority of cells in astrocytoma tumor regions (FIGS. 3A-3D, 3I). In CNS lymphoma, SR101 labeled a small number of cells in tumor regions (FIG. 3E). Some cells labeled by fixable-SR101 in lymphoma regions were not CD20 positive, and appeared to be reactive astrocytes based on morphology (FIGS. 3E, 3F, 3H arrows).

Statistically, the number of SR101 positive cells in astrocytoma regions did not differ from the number of GFAP positive cells (FIG. 3I). However, in lymphoma slices there were significantly more CD20 positive cells than fixable-SR101 positive cells (FIG. 3J). We compared antibody localization and found SR101 co-localized with 79.6% of GFAP-positive cells in astrocytoma regions, and co-localized with 1.97% of CD20 positive cells in lymphoma tumor regions ($p<0.001$) (FIG. 3K). This demonstrates SR101's strong co-localization to GFAP-positive cells in astrocytoma, and its ability to rapidly differentiate this astrocytic tumor from a non-astrocytic tumor such as CNS lymphoma.

Figure 4:
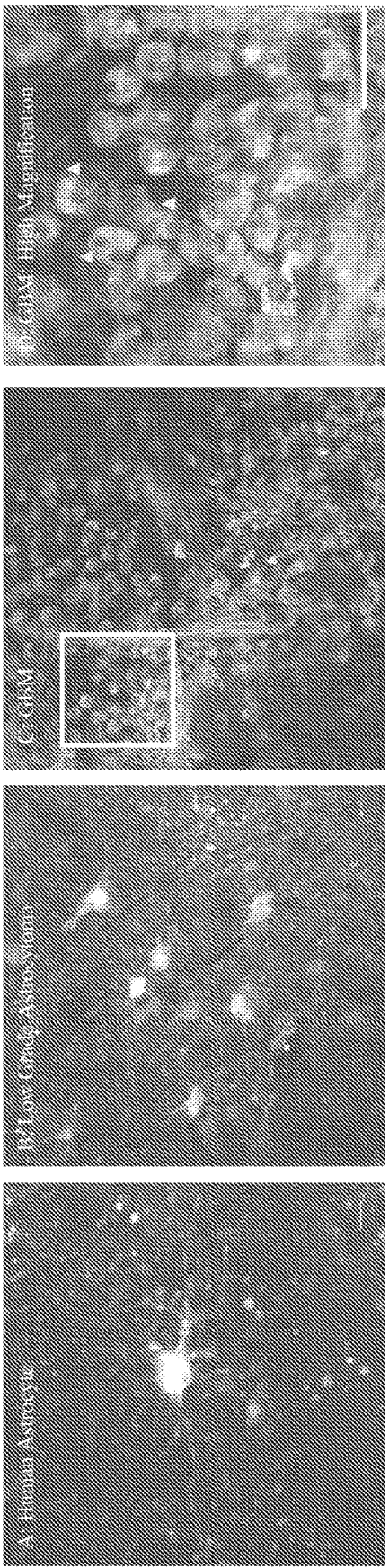
FIG. 4 depicts results showing that SR101 selectively labels human astrocytes and astrocytic brain tumors. Human brain tumor biopsies rapidly stained with SR101 and imaged with a confocal microscope. (A) Astrocyte from human brain labeled with SR101. (B) Low grade astrocytoma with morphologically distinct tumor cells and reactive astrocytes. (C) Grade IV astrocytoma. (D) Inset from C; hypercellularity and nuclei (arrowheads) are evident. (E-G) Non-astrocytic tumors absent of cells cytoplasmically filled with SR101. Dark regions in tissue indicate location of cell bodies. (H) Oligodendroglioma does not stain with SR101. (I) Lymphoma is negative for SR101 staining. Scale bar equals 20 um.
Figure 4:
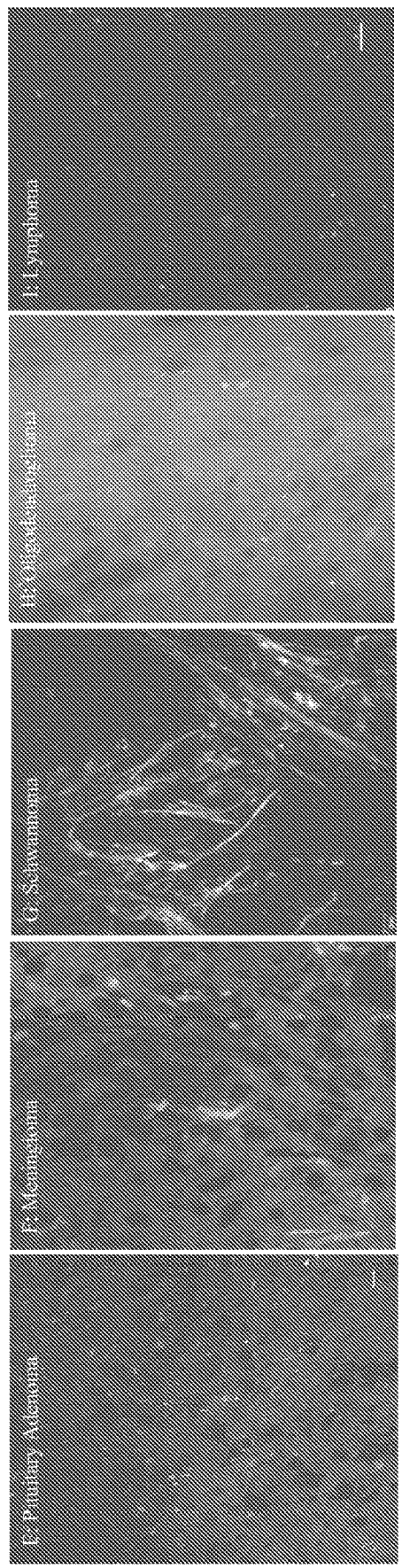
Figure 5:
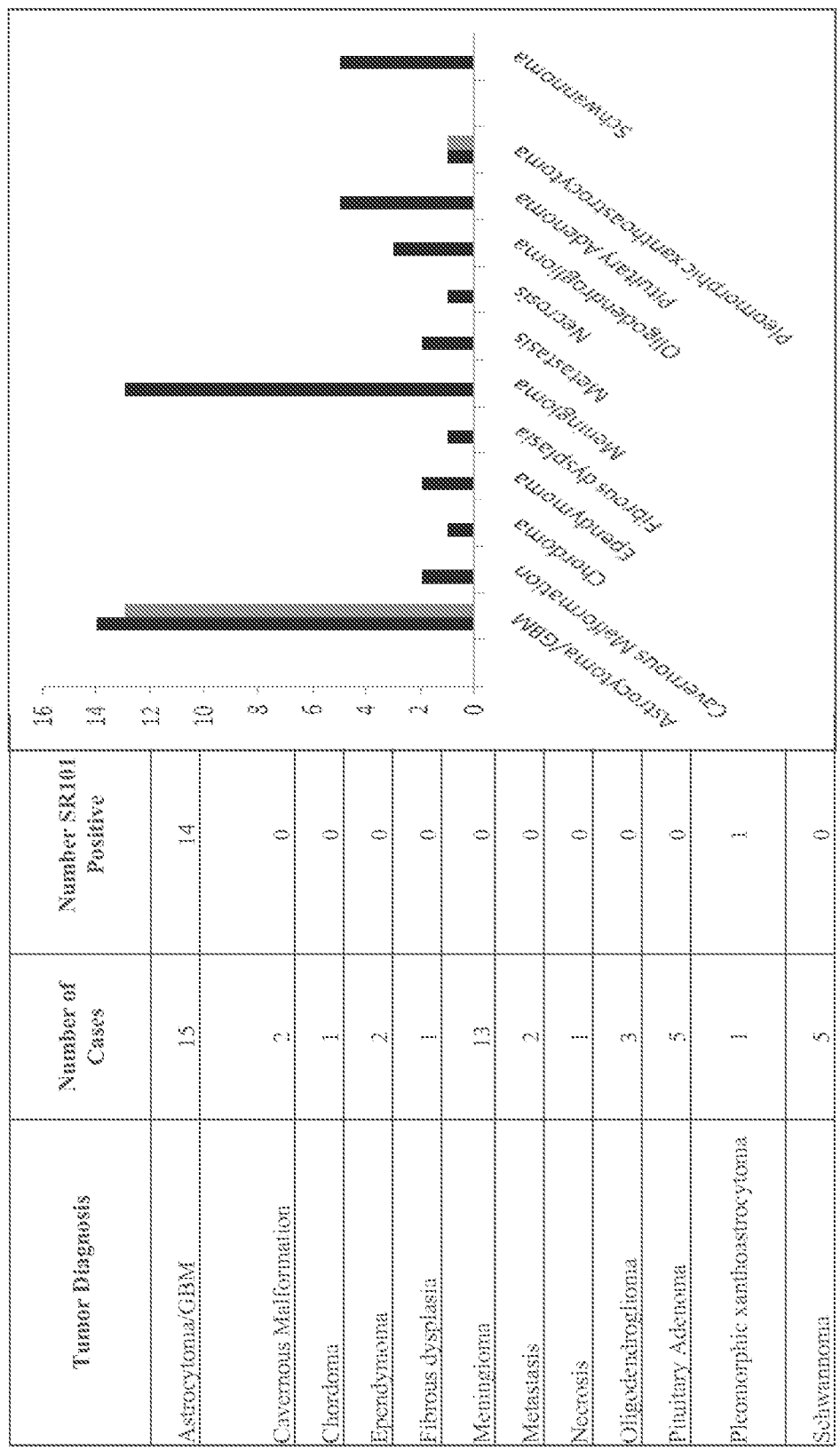
FIG. 5 depicts distribution of human biopsies stained with SR101 and final diagnosis. SR101 selectively stained 14 of 15 astrocytoma cases and a Pleomorphic Xanthoastrocytoma. SR101 did not stain tumors cells from additionally sampled CNS neoplasms.
Figure 6:
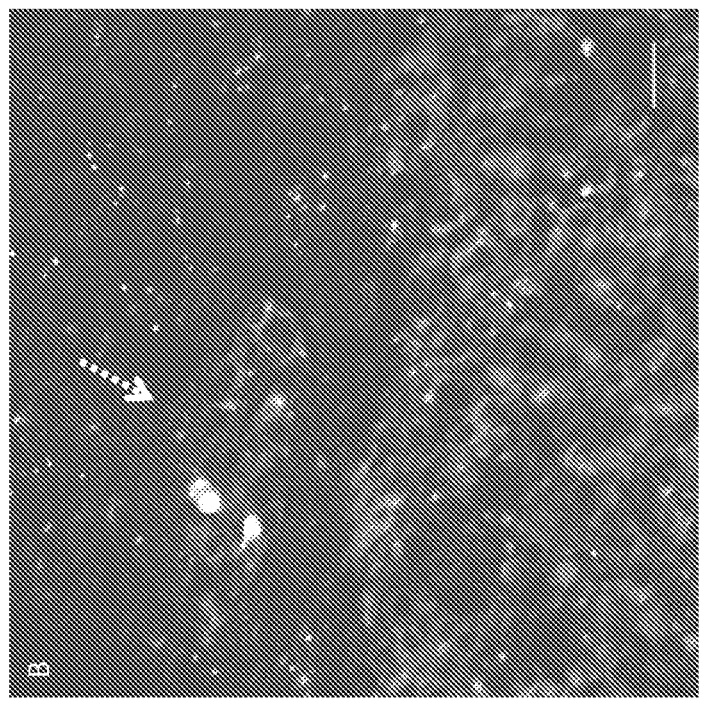
FIG. 6 depicts specific in vivo labeling of human glioma cells in a rodent xenograft after intra-arterial injection of fixable SR101. (A) Low magnification image shows SR101 labeling of tumor cells and the tumor margin (arrow). (B) High magnification image of the tumor margin shows labeling of infiltrative tumor cells (dashed arrow).
Figure 6:

SR101 Intraoperatively Differentiates Human Astrocytoma from Other Human CNS Neoplasms After we identified SR101's ability to rapidly label and differentiate astrocytoma cells and reactive astrocytes in animal models, we tested its utility as an intraoperative diagnostic agent. We determined the feasibility of intraoperatively identifying astrocytic brain tumors by confocal fluorescence imaging of fresh human brain tumor biopsies labeled with SR101. We screened samples from 60* patients with a total of 10 common human brain tumor types. The diagnosis as determined by traditional immunohistochemistry and paraffin-embedded hematoxylin and eosin histopathology was accepted as the final diagnosis for the purposes of comparison. Tissue samples were transported in artificial cerebrospinal fluid and imaged within 30-40 minutes of resection. We first found SR101 filled the cytoplasm of astrocytes in non-tumor burdened brain (FIG. 4A). Next, we studied tissue sampled from tumor margins and found SR101 filled the cytoplasm of reactive astrocytes and tumor cells in these regions (FIG. 4B). We also found strong cytoplasmic staining of cells from astrocytoma tumor cores (FIG. 4C). At higher magnification we observed that SR101 delineated some cell nuclei and identified nuclear atypia which is a common feature of some gliomas (FIG. 4C). In non-astrocytic tumor samples, SR101 produced non-specific background staining. In these tumor biopsies, SR101 outlined the location of cell bodies but did not provide cytoplasmic filling (FIGS. E-I).

Interestingly, SR101 did not label some low grade human oligodendroglioma samples which are often GFAP positive (FIG. 4H). In support of the animal model data, SR101 failed to stain human lymphoma (FIG. 4I). These data show SR101's specificity for human astrocytes, astrocytomas, and reactive astrocytes. SR101 staining coupled with confocal microscopy allows human astrocytic tumors and reactive astrocytes to be rapidly identified in a time frame that supports intraoperative decision-making.

We have demonstrated a technique for identifying the most common primary brain tumor by ex vivo exposure to the fluorescent dye sulforhodamine 101. This technique can be completed rapidly enough to provide the diagnosis while surgery is still in progress. In our study, we tested the specificity of SRIOI in human cell culture, orthotopic rodent xenografts, and human tumor samples. Compared to immunocytochemistry and final pathological paraffin-embedded diagnoses, SR101 provided more rapid and equally accurate identification of astrocytic tumors in all model systems. In human samples, SR101 provided effective visualization and differentiation of astrocytic tumors and their margins.

Improvements in timely and accurate intraoperative diagnoses are a profound need in clinical neurosurgery. Current diagnostic techniques rely on visualization of tissue with standard light microscopes and conventional contrast agents, a technique which has evolved little over the last 100 years. Here, we have shown fluorescent labeling of ex vivo tissue coupled with confocal imaging can provide clear benefits compared with current diagnostic techniques. Our technique allows visualization of pathological tissue without freezing, fixation, or sectioning. Images collected from tissue can provide a diagnosis in a time frame to guide patient care while surgery is still in progress.

Figure 7:
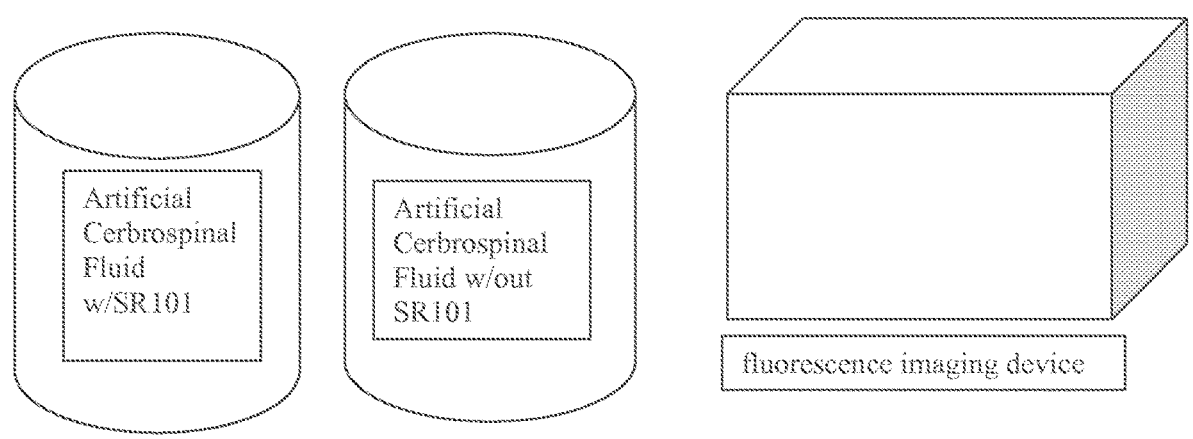
FIG. 7 depicts a system or kit to facilitate rapid inoperative determination of an astrocytic human brain tumor from a non-astrocytic human brain tumor.

We envision that fluorescence imaging of ex vivo tissue will become a commonplace technique in modernized pathology departments. We identified an example of an immediate benefit this diagnostic modality can provide anatomical pathology; the differentiation of high grade astrocytoma from CNS lymphoma. These tumors present with similar macroscopic appearance during resection, and their treatment plans are markedly distinct. Astrocytomas require maximal safe resection to provide survival benefits to patients, while lymphomas are best biopsied and treated with adjuvant therapy. Differentiating these tumors requires a surgical biopsy followed by a minimum of 24 hours for diagnostic processing. We found these tumors could be differentiated by SR101 staining and confocal microscopy within 30 minutes of biopsy. This information could allow rapid modification to the surgical plan with consequent improvement of outcomes. Thus, a system or kit to facilitate rapid intraoperative determination of an astrocytic human brain tumor from a non-astrocytic human brain tumor is provided (FIG. 7). The kit contains, a container having ice-cold artificial cerebrospinal fluid containing SR101, a container having ice cold artificial cerebrospinal fluid without SR101, and a substrate for placing the tissue during staining/imaging. The system adds a fluorescence imaging device.

Probes and devices that allow microscopic visualization and diagnosis of deep in vivo structures are currently under development. Some in vivo fluorescence imaging instruments have already been clinically tested (Confocal, FLIM, Optiscan). However, due to safety concerns, some fluorophores and imaging modalities may never be approved for in vivo clinical use. We believe rapid ex vive diagnostics will compliment in vivo imaging by providing information from tissues processed with techniques that may not safe for in vivo clinical use.

It is understood that, in addition to using the confocal microscopy system, as discussed in the above examples, the SR101 fluorophore can be imaged with any fluorescent microscope such as, for example, Widefield/Epifluorescent or Multiphoton microscopy system. The fluorophore can be used in vivo (topical and injectable) as well as in ex vivo, and at various concentrations. In one experiment, concentration of 0.5 uM to 1 mM were successfully tested, with higher concentrations useful for an in-vivo use. This fluorophore is deemed to facilitate clinical differentiation of human oligodendroglioma from astrocytoma. Such differentiation is not currently possible with standard pathology approaches using antibody (GFAP) staining.

There are liabilities to diagnostic use of Sulforhodamine 101. Staining with this agent requires tissue to be alive and relatively healthy when it is incubated with the dye. Damaged cells have been reported to uptake the dye. However, we did not encounter significant false positives in our experiments. A practical limitation to the widespread use of SR101 includes solutions being available in the operating room for immediate incubation of resected tissue. Presently, immediate ex vivo imaging using specific fluorescent probes is not part of clinical pathological practice. Therefore, confocal microscopes are not found in most pathology laboratories. We believe these limitations will be overcome with modernization of pathology departments.

To our knowledge, our results provide the first use of a functional dye on living human brain tumor tissue to provide a clinically meaningful immediate ex vivo histopathological diagnosis. Various modifications are possible within the meaning and range of equivalence of the appended claims.

The invention claimed is:

1. A method for differentially imaging an astrocytic human brain tumor from a non-astrocytic human brain tumor without immunostaining, comprising the steps of:
    staining with sulforhodamine 101 (SR101) brain tumor tissue from a human subject with a brain tumor of an unknown type; and
    imaging said brain tumor tissue stained with SR101 with a fluorescence imaging device to confirm either an astrocytic tumor type or a non-astrocytic tumor type, wherein said astrocytic tumor type or said non-astrocytic tumor type are differentially imaged according to cytoplasmic staining for the astrocytic tumor type and a lack of cytoplasmic staining for the non-astrocytic tumor type.

2. The method of claim 1, wherein said tumor tissue from the subject is stained ex vivo.

3. The method of claim 1, wherein said non-astrocytic human brain tumor is an oligodendroglioma.

4. The method of claim 1, wherein said non-astrocytic human brain tumor is a Central Nervous System (CNS) lymphoma.

5. The method of claim 1, wherein said staining and imaging steps are performed intraoperatively.

* * * * *